(12) United States Patent
Terranova et al.

(10) Patent No.: US 7,319,155 B2
(45) Date of Patent: Jan. 15, 2008

(54) 7,7-DISUBSTITUTED (5H,9H)-6,8-DIOXABENZOCYCLOHEPTENE COMPOUNDS USEFUL IN THE SYNTHESIS OF NON-STEROIDAL ANALOGUES OF VITAMIN D

(75) Inventors: Eric Terranova, Magagnosc (FR); Jean-Claude Pascal, Nice (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 11/598,784

(22) Filed: Nov. 14, 2006

(65) Prior Publication Data

US 2007/0117989 A1    May 24, 2007

Related U.S. Application Data

(63) Continuation of application No. PCT/FR2005/001210, filed on May 13, 2005.

(60) Provisional application No. 60/577,201, filed on Jun. 7, 2004.

(30) Foreign Application Priority Data

May 14, 2004    (FR)    .................... 04 05282

(51) Int. Cl.
  *C07D 321/00*    (2006.01)
  *C07D 323/00*    (2006.01)
  *C07D 317/72*    (2006.01)
  *C07C 33/18*    (2006.01)
  *C07C 33/34*    (2006.01)

(52) U.S. Cl. .................... 549/350; 549/336; 568/715

(58) Field of Classification Search ............... 549/350, 549/336; 568/715

See application file for complete search history.

(56) References Cited

U.S. PATENT DOCUMENTS 6,235,731 B1 *  5/2001  Shibouta et al. ......... 514/224.5
6,831,106 B1    12/2004 Bernardon et al.
6,924,400 B2    8/2005  Bernardon et al.

FOREIGN PATENT DOCUMENTS

WO    WO 01/38303 A2    5/2001
WO    WO 03/050067 A2   6/2003

* cited by examiner

*Primary Examiner*—Janet Andres
*Assistant Examiner*—Niloofar Rahmani
(74) *Attorney, Agent, or Firm*—Buchanan, Ingersoll & Rooney, PC

(57) ABSTRACT

Novel 7,7-disubstituted (5H,9H)-6,8-dioxabenzocycloheptene compounds having the structural formula (I):

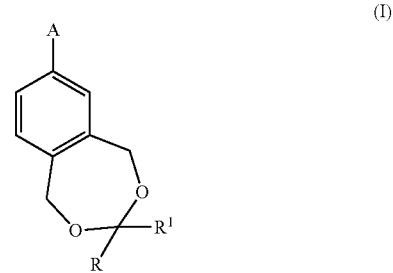

are useful intermediates in the synthesis of non-steroidal derivatives of vitamin D.

26 Claims, 4 Drawing Sheets

- Scheme A: Synthesis of non-steroidal analogues (IV) of vitamin D -

- Scheme A': Synthesis of non-steroidal analogues (IV') of vitamin D -

7,7-DISUBSTITUTED (5H,9H)-6,8-DIOXABENZOCYCLOHEPTENE COMPOUNDS USEFUL IN THE SYNTHESIS OF NON-STEROIDAL ANALOGUES OF VITAMIN D

CROSS-REFERENCE TO PRIORITY/PCT/PROVISIONAL APPLICATIONS

This application claims priority under 35 U.S.C. § 119 of FR 04/05282, filed May 14, 2004, and of Provisional Application No. 60/577,201, filed Jun. 7, 2004, and is a continuation of PCT/FR2005/001210 filed May 13, 2005 and designating the United States, published in the French language as WO 2005/116007 A1 on Dec. 8, 2005 (the title and Abstract were also published in English), each hereby expressly incorporated by reference and each assigned to the assignee hereof.

BACKGROUND OF THE INVENTION

Technical Field of the Invention

The present invention relates to novel 7,7-disubstituted (5H,9H)-6,8-dioxabenzocycloheptene compounds, methods for the preparation thereof and their use in the synthesis of non-steroidal analogues of vitamin D.

SUMMARY OF THE INVENTION

The present invention features novel 7,7-disubstituted (5H,9H)-6,8-dioxabenzocycloheptene compounds having the following structural formula (I):

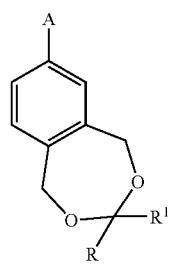

(I)

in which:
 A is a radical —CH$_2$—Y or a carboxaldehyde group —C(=O)H;
 Y is a halogen atom, advantageously a chlorine or bromine atom, a hydroxyl radical, a radical —OSO$_2$R$^2$, or a radical P(O)(OR$^3$)$_2$;
 R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being selected from a chlorine, bromine, iodine or fluorine atom, an alkyl radical, an alkoxy radical, a cyano group and a nitro group;
 with the proviso that R and R$^1$ may together form, with the carbon atom from which they depend, a ring member of 5 or 6 carbon atoms;
 R$^2$ is an alkyl radical or an aryl radical; and
 R$^3$ is an alkyl radical;

and the optical isomers thereof.

In particular, the compounds of general formula (I) will be such that R and R$^1$ cannot simultaneously be a methyl radical when A is the radical —CH$_2$OH.

The expression alkyl radical means a linear or branched alkyl radical having from 1 to 4 carbon atoms, and in particular methyl, ethyl, propyl, isopropyl, 2-methylpropyl, butyl, sec-butyl and tert-butyl radicals.

Likewise, the expression alkoxy radical means a linear or branched alkoxy radical having from 1 to 4 carbon atoms, and in particular methoxy, ethoxy, propoxy, isopropoxy, butoxy, sec-butoxy and tert-butoxy radicals.

The expression aryl radical means phenyl, naphthyl or pyridyl.

The expression ring of 5 or 6 carbon atoms means a cyclopentane radical or a cyclohexane radical.

DETAILED DESCRIPTION OF BEST MODE AND SPECIFIC/PREFERRED EMBODIMENTS OF THE INVENTION

According to the present invention, the preferred compounds of formula (I) are those in which A is a radical —CH$_2$—Y, wherein Y is a chlorine or bromine atom or a radical OSO$_2$R$^2$ or a radical P(O)(OR$^3$)$_2$, and R is a hydrogen atom and R$^1$ is a nitrophenyl radical or conversely for R and R$^1$.

According to the present invention, the preferred compounds are also those in which A is a radical —CH$_2$—Y, wherein Y is a hydroxyl radical, R is a hydrogen atom and R$^1$ is a nitrophenyl radical or conversely for R and R$^1$.

Among the compounds of formula (I), preferably at least one of R or R$^1$ does not represent hydrogen.

The present invention also features methods for preparing the compounds of structural formula (I) via the following reaction scheme.

Figure 1:
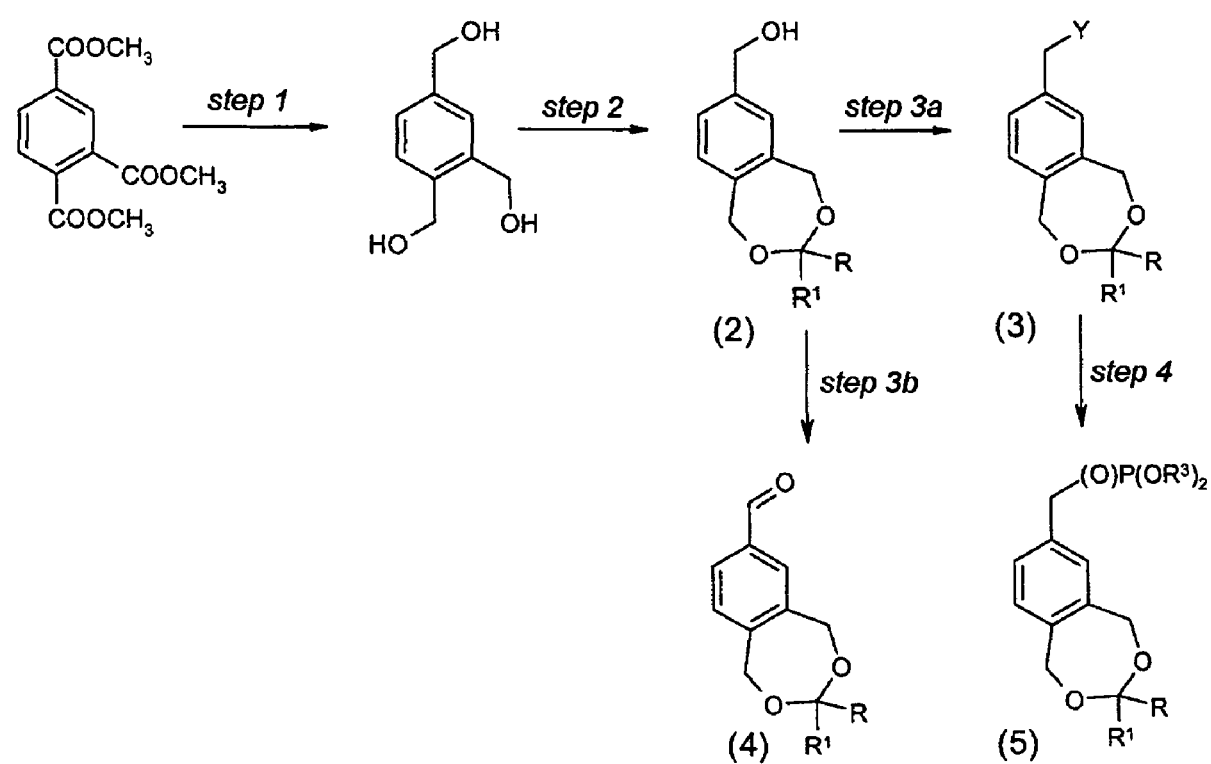
FIG. 1 illustrates reaction schemes according to the present invention for the preparation of the compounds having the structural formula (I)

According to the present reaction scheme shown in FIG. 1, the compounds of general formula (I) may be prepared from a trialkyl ester of 1,2,4-benzenetricarboxylic acid according to the following steps:
 in step 1, a trialkyl ester of 1,2,4-benzenetricarboxylic acid, for example trimethyl 1,2,4-benzenetricarboxylate, is subjected to a reduction reaction, as described for example in Nakazaki, M.; Yamamoto, K. and Miura, Y.; *J. Org. Chem.*, 43(6), (1978), 1041-1044, for example by means of lithium borohydride, in an aprotic solvent, such as tetrahydrofuran, to give (3,4-bis-hydroxymethylphenyl)methanol,
 in step 2, the said (3,4-bis-hydroxymethylphenyl)methanol is itself subjected to a reaction for selective protection of the two adjacent benzyl alcohol functional groups at the 3 and 4 positions by reaction with a ketone or an aldehyde of formula R—CO—R$^1$, in an aprotic solvent, such as for example dichloromethane, in the presence of a catalyst, advantageously of zeolite, such as the zeolite HZSM-5 or the zeolite HY, as described for example by Tajbakhsh, M. et al. (*Synth. Commun.*, (1999), 29(1), 135-138) or, alternatively, by Kumar, T. P. et al. (*J. Chem. Res. Synop.*, (1994), 10, 394-395), or the zeolite EPZG, as described by Bandgar, B. P. et al. (*Synth. Commun.*, (1997), 27(4), 627-634), or, alternatively, in the presence of catalytic quantities of montmorillonite KSF, as described by Patney, H. K. (*Synth. Commun.*, (1993), 23(11), 1523-1526), to give the compounds of general formula (2):

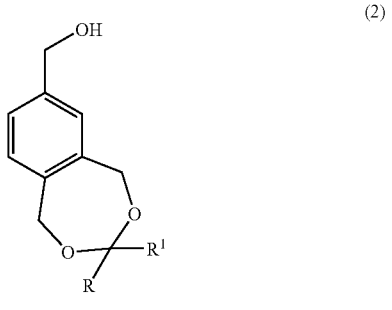
(2)

in step 3(a), the compounds of formula (2) thus obtained may then, by reaction with a derivative $R^2SO_2Cl$, be converted to compounds of formula (3):

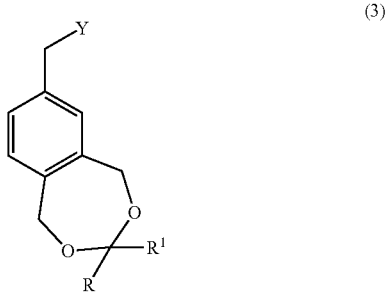
(3)

in which Y, according to the reaction conditions, is a halogen atom, selected from a chlorine or bromine atom, or a group $-OSO_2R^2$, in step 4, the compounds of formula (3) defined above and in which Y is a halogen atom, selected from a chlorine or bromine atom, may in turn be converted to compounds of formula (5):

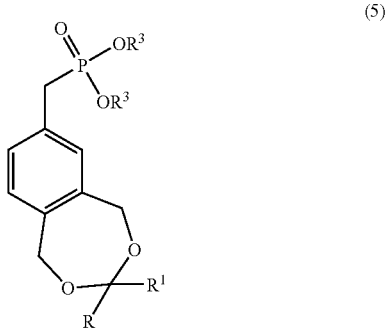
(5)

by reaction with a trialkylphosphite derivative $P(OR^3)_3$, according to a similar method to that described by Moreau, B. et al. (*Org. Prep. Proced. Int.*, (2002), 34(5), 539-542).

According to the reaction scheme presented in FIG. 1, the compounds of general formula (I) may also be prepared from a trialkyl ester of 1,2,4-benzenetricarboxylic acid according to the same steps 1 and 2, and in step 3(b), the compounds of formula (2) may be used in an oxidation reaction, by the action of an oxidizing agent such as manganese oxide or pyridinium chlorochromate, to give the compounds of formula (4):

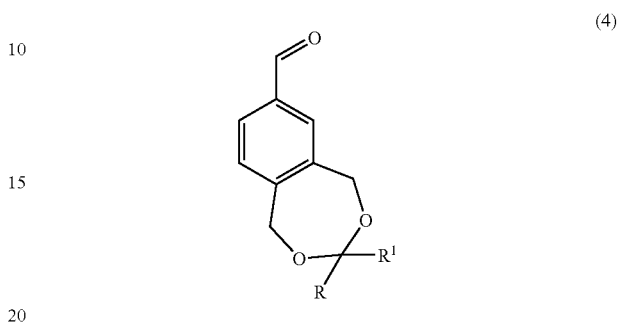
(4)

the compounds of formulae (2), (3), (4) and (5) together representing the entirety of the compounds of formula (I) defined above and which are the subject of the invention.

It is understood, unless otherwise stated, in the preceding text that Y, R, $R^1$, $R^2$ and $R^3$ are as defined in formula (I).

The raw materials used for the preparation of the compounds of formula (I) according to the invention are commercially available or can be easily obtained from commercially available raw materials, according to methods which are known or derived from methods which are known and known to a one skilled in the art or easily accessible from the patent literature or from scientific articles, from Chemical Abstracts and the Internet.

According to another aspect of the present invention, the compounds of general formula (I) are useful as intermediates for the synthesis of non-steroidal analogues of vitamin D.

In WO 03/050067 is described the introduction of the moiety mimicking ring A of the non-steroidal analogues of vitamin D either by coupling of the dimethyl ester of 4-bromomethylphthalic acid, prepared in three steps from trimellitic anhydride, or by reaction of (3,4-bis-benzoyloxymethyl)benzyl bromide prepared in 7 steps, also from trimellitic anhydride, or, alternatively, by reaction of the dimethyl ester of 4-(diethoxyphosphorylmethyl)phthalic acid, prepared in 4 steps from trimellitic anhydride. In the cases where a phthalic acid derivative is employed, the final step entails a reduction of the two ester functional groups.

The present invention also features the methods for preparing novel 7,7-disubstituted (5H,9H)-6,8-dioxabenzocycloheptene derivatives of formula (I) which have the advantage of offering a novel method for synthesizing non-steroidal analogues of vitamin D such as those described in WO 03/050067. Preferably, after coupling with a biphenyl moiety, the compounds of formula (I) make it possible to obtain the compounds of formula (III) as defined and presented in FIG. 2, and then, in a dilute acid medium or by hydrogenolysis in the presence of a catalytic quantity of platinum or palladium oxide make it possible to obtain the compounds of general formula (IV), as defined below.

These compounds, prepared in only three or four steps, therefore constitute novel and useful intermediates in the synthesis of non-steroidal analogues of vitamin D.

In particular, the compounds of formula (I) of the present invention offer the advantage of obtaining non-steroidal analogues of vitamin D via a method comprising a lesser number of steps compared to the methods described in the prior art, and involving simple and selective protection and deprotection steps.

Thus, the present invention also features the use of the 7,7-disubstituted (5H,9H)-6,8-dioxabenzocycloheptene derivatives of formula (I) as defined above, and in particular the compounds (2), (3), (4) and (5) defined above, as synthesis intermediates, for the preparation of non-steroidal derivatives of vitamin D.

Preferably, the compounds of formula (I), in particular the compounds (2), (3), (4) and (5) according to the invention, are used as intermediates for the synthesis of non-steroidal derivatives of vitamin D. In the remainder of the present disclosure, it will be understood that formula (I) includes all the compounds of formulae (2), (3), (4) and (5) and that the compounds of formulae (2), (3), (4) and (5) correspond to the compounds of formula (I).

More preferably, the compounds of formula (I), in particular the compounds (2), (3), (4) and (5) according to the invention, are used as intermediates for the synthesis of non-steroidal derivatives of vitamin D corresponding to the following formula (IV):

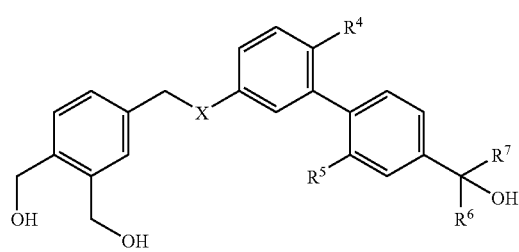

in which:
R$^4$ and R$^5$, which may be identical or different, are each a linear or branched alkyl radical having from 1 to 3 carbon atoms;
R$^6$ and R$^7$, which may be identical, are each a linear or branched alkyl radical having from 1 to 2 carbon atoms, hydrogenated or perfluorinated;
X is —CH$_2$—, —NH—, —NR$^8$— or —O— and
R$^8$ is a linear or branched alkyl radical having from 1 to 3 carbon atoms.

The expression alkyl radical having from 1 to 3 carbon atoms according to the present invention means a methyl radical, an ethyl radical, a propyl radical or an isopropyl radical.

The expression alkyl radical having from 1 to 2 carbon atoms, hydrogenated or perfluorinated, according to the present invention means an ethyl radical or a trifluoromethyl radical.

Figure 2:
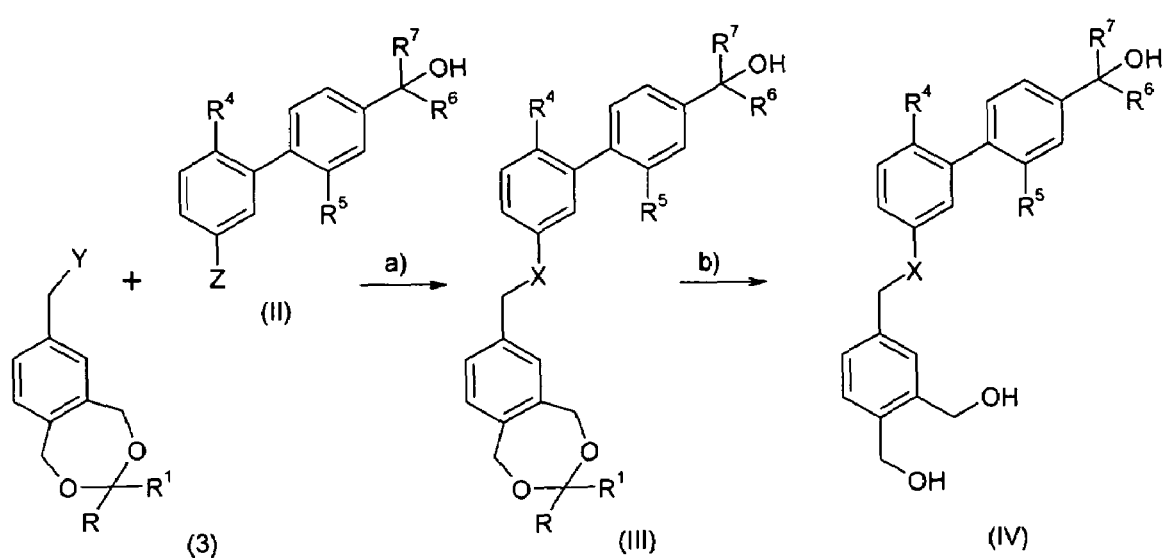
FIGS. 2-4 illustrate several reaction schemes for the synthesis of non-steroidal analogues of vitamin D, starting with the compounds of structural formula (I).

According to a preferred embodiment of the present invention, the compounds of formula (3) according to the invention are involved in the synthesis of non-steroidal analogues of vitamin D, which correspond to formula (IV) as defined above, according to scheme A presented in FIG. 2, in which scheme Y is a halogen atom, selected from a chlorine or bromine atom, or a radical —OSO$_2$R$^2$, Z is a hydroxyl radical, or a radical —NHR$^8$, R$^8$ representing a linear or branched alkyl radical having 1 to 3 carbon atoms, R, R$^1$, R$^4$, R$^5$, R$^6$, R$^7$ and X are as defined above:

step a) corresponding to a reaction for coupling of the compound of formula (3) of the present invention:

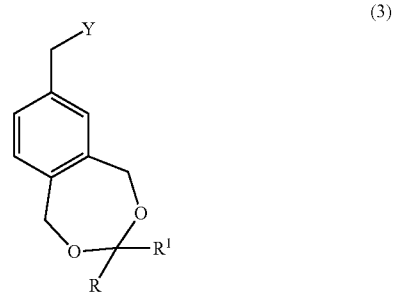

with a compound of formula (II):

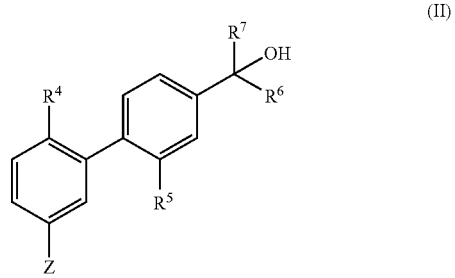

namely, by coupling reaction from the two reactive functional groups —CH$_2$—Y— and Z leading to the formation of a bond —CH$_2$—X—, Y and X being as defined above, for the production of a compound of formula (III):

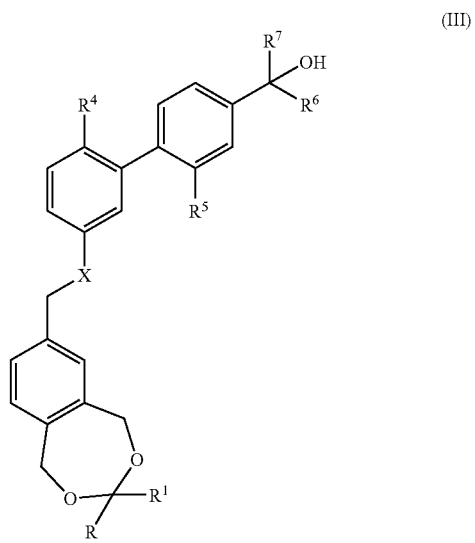

step b) corresponding to a conventional reaction for deprotection of the two adjacent benzyl alcohol functional groups at the 3 and 4 positions contained in the (5H,9H)-6,8-dioxabenzocycloheptene ring of the compound of formula (III), the said ring being obtained from the compound of formula (3), for the production of the compound of formula (IV):

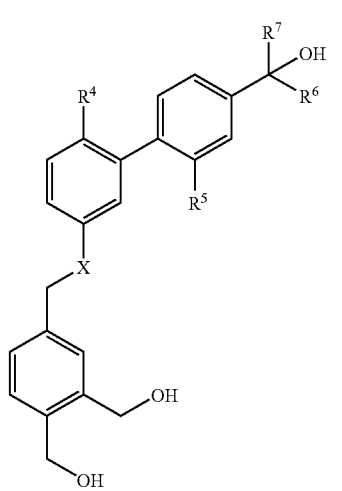

(IV)

Figure 3:
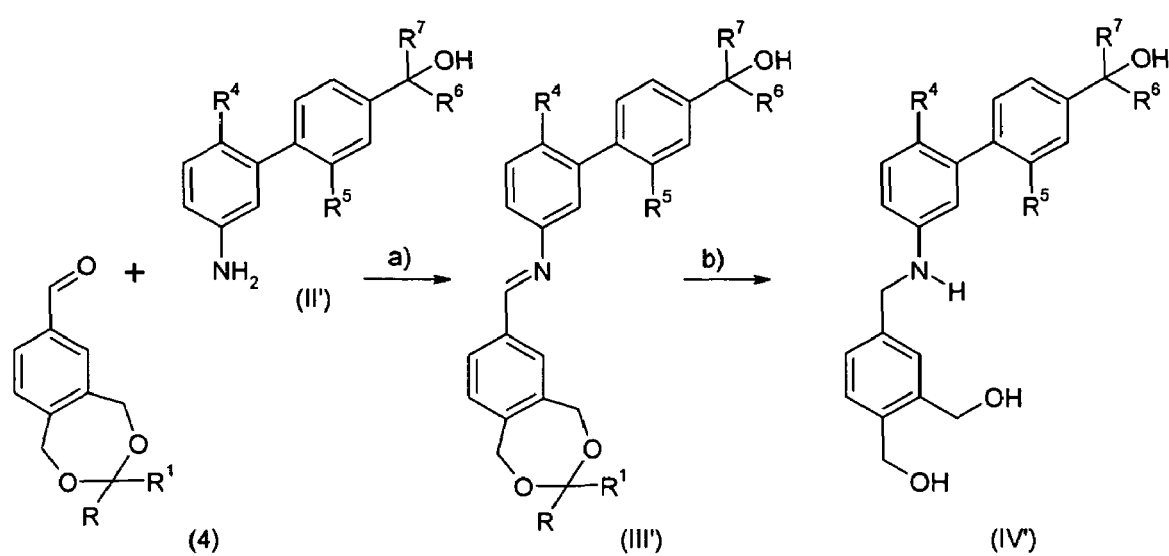

According to another preferred embodiment of the present invention, the non-steroidal analogues of formula (IV'), in which analogues of formula (IV) X is —NH—, may be advantageously prepared from the compounds of formula (4) according to the invention and compounds of formula (II'), namely, compounds of formula (II) where Z is —NH$_2$, according to scheme A' presented in FIG. 3, in which scheme R, R$^1$, R$^4$, R$^5$, R$^6$ and R$^7$ are as defined above:

step a) corresponding to a conventional coupling reaction from the aldehyde functional group of the compound of formula (4):

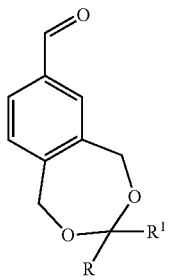

(4)

and the amine functional group of the compound of formula (II'):

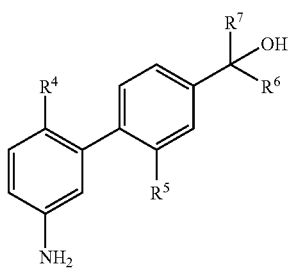

(II')

for the production of the compound of formula (III'):

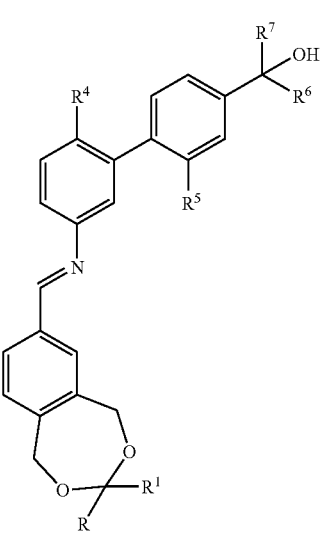

(III')

step b) being a hydrogenation and hydrogenolysis reaction on the compound of formula (III'), allowing, in a single step, both the reduction of the imine functional group (hydrogenation) and the deprotection of the two adjacent benzyl alcohol functional groups at the 3 and 4 positions contained in the (5H,9H)-6,8-dioxabenzocycloheptene ring obtained from the compound of formula (4) (hydrogenolysis), for the production of the compound of formula (IV'):

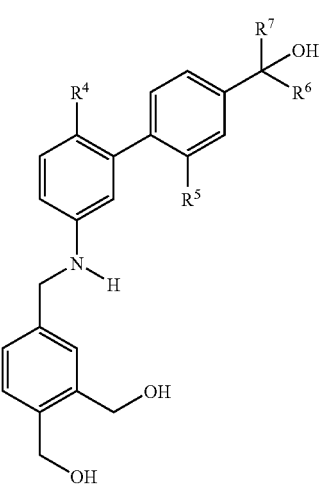

(IV')

Figure 4:
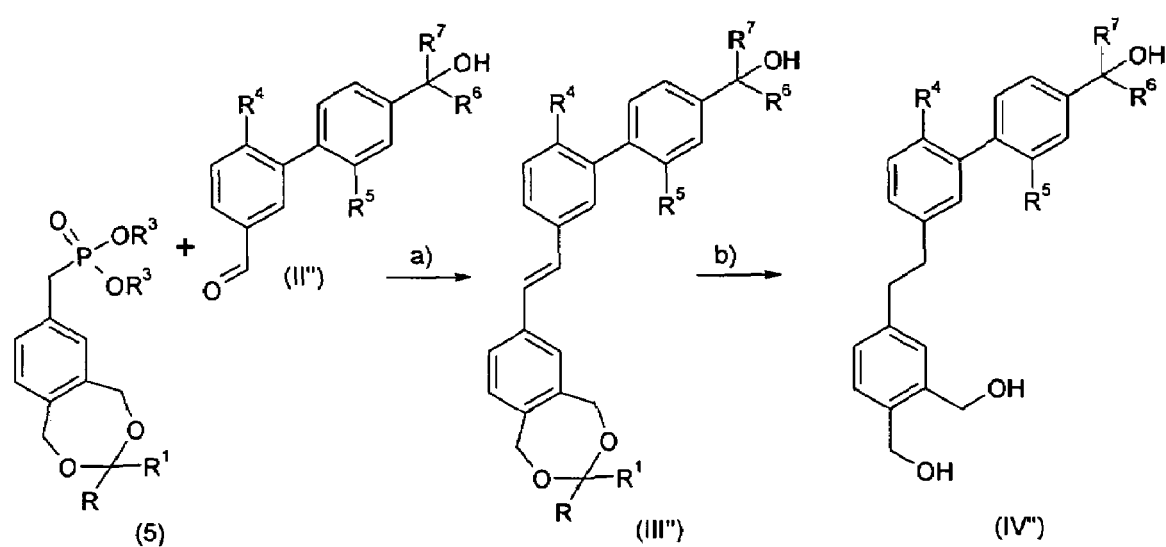

According to another preferred embodiment of the present invention, the non-steroidal analogues of formula (IV''), in which analogues of formula (IV) X is —CH$_2$—, may be advantageously prepared from the compounds of formula (5) according to the invention and the compounds of formula (II''), namely, the compounds of formula (II) where Z is a carboxaldehyde group —C(=O)H, according to the scheme A'' presented in FIG. 4 in which scheme R, R$^1$, R$^3$, R$^4$, R$^5$, R$^6$ and R$^7$ are as defined above:

step a) corresponding to a conventional so-called Horner-Emmons reaction from the compound of formula (5):

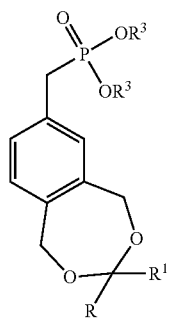

and the compound of formula (II''):

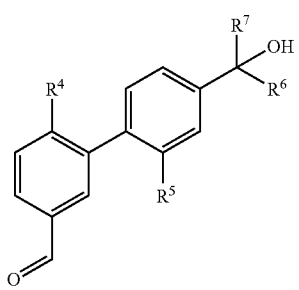

for the production of the compound of formula (III''):

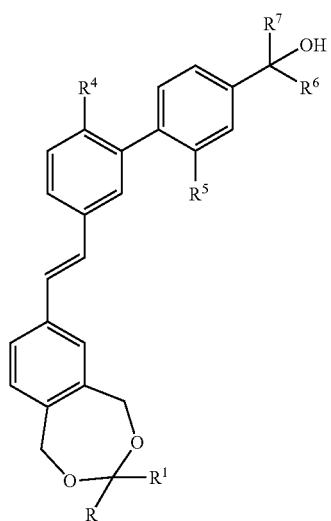

step b) being a hydrogenation and hydrogenolysis reaction on the compound of formula (III''), allowing, in a single step, both the reduction of the double bond (hydrogenation) and the deprotection of the two adjacent benzyl alcohol functional groups at the 3 and 4 positions contained in the (5H,9H)-6,8-dioxabenzocycloheptene ring obtained from the compound of formula (5) (hydrogenolysis), for the production of the compound of formula (IV''):

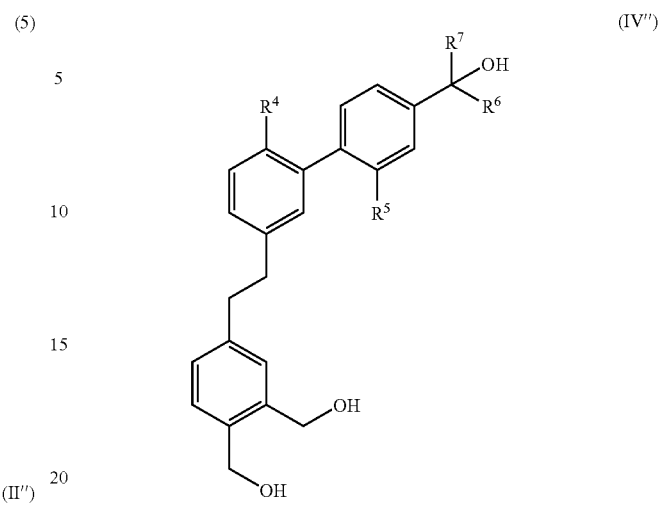

The present invention therefore also features the use of the compounds of general formula (II):

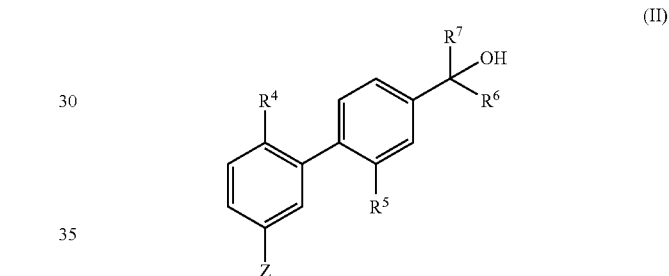

for the preparation of non-steroidal analogues of vitamin D of general formula (IV):

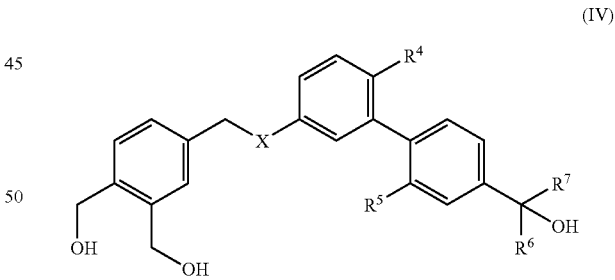

in which
  $R^4$ and $R^5$, which may be identical or different, are each a linear or branched alkyl radical having from 1 to 3 carbon atoms;
  $R^6$ and $R^7$, which may be identical, are each a linear or branched alkyl radical having from 1 to 2 carbon atoms, hydrogenated or perfluorinated;
  X is —$CH_2$—, —NH—, —$NR^8$— or —O— and
  $R^8$ is a linear or branched alkyl radical having from 1 to 3 carbon atoms.

According to another of its aspects, the present invention features the use of the compounds of general formula (II'):

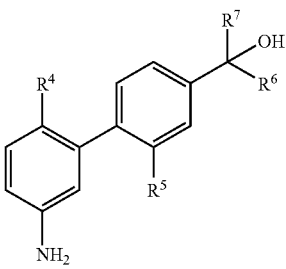

(II')

for the preparation of non-steroidal analogues of vitamin D of general formula (IV'):

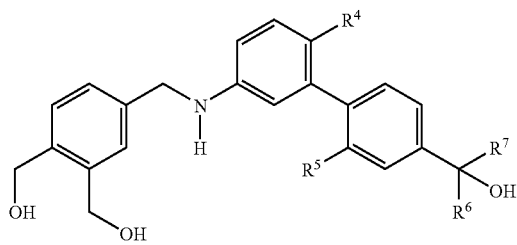

(IV')

in which:
- R⁴ and R⁵, which may be identical or different, are each a linear or branched alkyl radical having from 1 to 3 carbon atoms;
- R⁶ and R⁷, which may be identical, are each a linear or branched alkyl radical having from 1 to 2 carbon atoms, hydrogenated or perfluorinated.

Finally, the present invention also features the use of the compounds of general formula (II'')

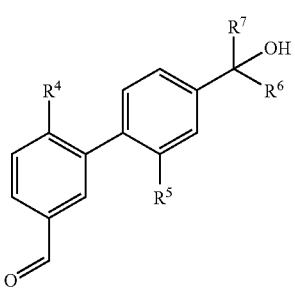

(II'')

for the preparation of non-steroidal analogues of vitamin D of general formula (IV'):

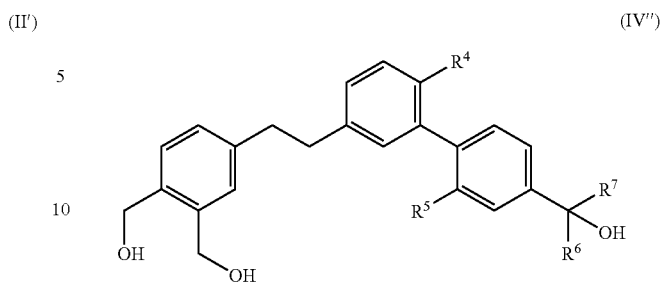

(IV'')

in which:
- R⁴ and R⁵, which may be identical or different, are each a linear or branched alkyl radical having from 1 to 3 carbon atoms;
- R⁶ and R⁷, which are identical, are an alkyl radical having from 1 to 2 carbon atoms, hydrogenated or perfluorinated.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Preparation of [7-(4-nitrophenyl)-(5H,9H)-6,8-dioxabenzocyclohepten-2-yl]methanol

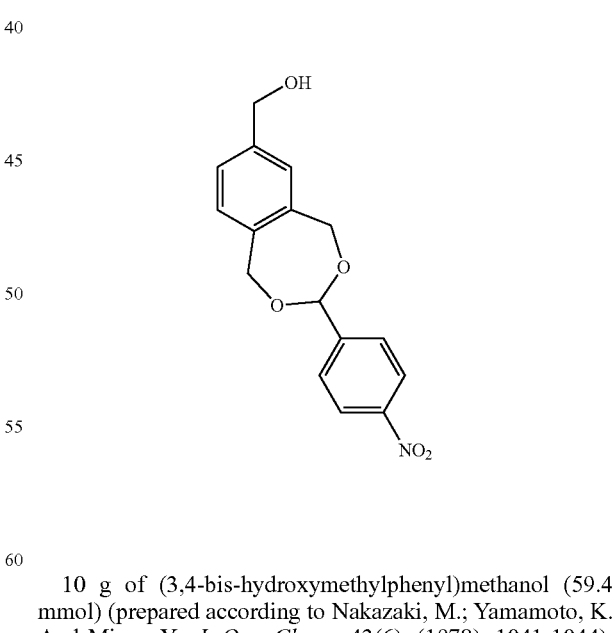

10 g of (3,4-bis-hydroxymethylphenyl)methanol (59.4 mmol) (prepared according to Nakazaki, M.; Yamamoto, K. And Miura, Y.; *J. Org. Chem.*, 43(6), (1978), 1041-1044), 100 ml of toluene, 8.98 g of 4-nitrobenzaldehyde (59.4 mmol) and 0.6 g of Montmorillonite KSF (10 mg/mmol) are introduced into a flask equipped with a Dean-Stark. The mixture is heated under reflux for 2 hours 30 minutes. The montmorillonite is filtered off and the reaction medium is allowed to return to room temperature, with stirring. The reaction product crystallizes. After filtration and drying under vacuum at 50° C., 11.2 g of [7-(4-nitrophenyl)-(5H,9H)-6,8-dioxabenzocyclohepten-2-yl]methanol are obtained.

Yield=58% Melting point=146° C. $^1$H NMR (DMSO d$_6$; 400.132 MHz) δ (ppm): 4.49 (d; 2H; J=5.6 Hz); 4.91 (d; 2H; J=14.1 Hz); 5.13 (dd; 2H; J=5.7 Hz and J=14.1 Hz); 5.20 (t; 1H; J=5.6 Hz); 6.12 (s; 1H); 7.24 (m; 3H); 7.73 (d; 2H; J=8.7 Hz); 8.24 (dd; 2H; J=1.9 Hz and J=7.0 Hz).

Example 2

Preparation of (7,7-spirocyclohexyl-(5H,9H)-6,8-dioxabenzocyclohepten-2-yl)methanol

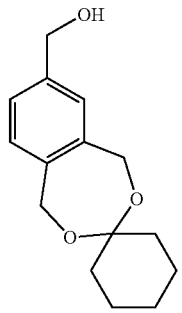

4 g of (3,4-bis-hydroxymethylphenyl)methanol (23.8 mmol), 50 ml of toluene, 2.57 g of cyclohexanone (26.2 mmol) and 0.24 g of Montmorillonite KSF (10 mg/mmol) are introduced into a flask equipped with a Dean-Stark. The reaction medium is heated under reflux for 2 hours 30 minutes. After filtration of the montmorillonite, the toluene is evaporated under vacuum at 30° C. 5.4 g of the expected crude product are obtained. After chromatography on silica gel (heptane/ethyl acetate=3/2), 1.3 g of (7,7-spirocyclohexyl)-(5H,9H)-6,8-dioxabenzocyclohepten-2-yl]methanol are obtained.

Yield=22% Melting point=96-98° C. $^1$H NMR (DMSO d$_6$; 400.132 MHz) δ (ppm): 1.40 (m; 2H); 1.50 (m; 4H); 1.72 (m; 4H); 4.44 (d; 2H; J=5.7 Hz); 4.77 (s; 2H); 4.78 (s; 2H); 5.13 (t; 1H; J=5.7 Hz); 7.06 (m; 3H).

Example 3

Preparation of (7-methoxy-(5H,9H)-6,8-dioxabenzocyclohepten-2-yl)methanol

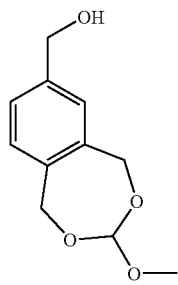

4 g of (3,4-bis-hydroxymethylphenyl)methanol (23.8 mmol), 40 ml of 1,2-dimethoxyethane, 2.78 g of methyl orthoformate (26.2 mmol) and 0.24 g of Montmorillonite KSF (10 mg/mmol) are introduced into a flask. The reaction medium is stirred at room temperature for 4 hours 30 minutes and then the montmorillonite is filtered off and the 1,2-dimethoxyethane is evaporated under vacuum at 30° C. The residue is chromatographed on silica gel (dichloromethane/methanol=98/2) to give 3.2 g of (7-methoxy)-(5H,9H)-6,8-dioxabenzocyclohepten-2-yl)methanol in the form of an oil.

Yield=64% $^1$H NMR (DMSO d$_6$; 400.132 MHz) δ (ppm): 3.35 (s; 3H); 4.46 (d; 2H; J=5.7 Hz); 4.66 (d; 2H; J=14.9 Hz); 4.94 (dd; 2H; J=5.9 Hz and J=14.8 Hz); 5.16 (t; 1H; J=5.7 Hz); 7.13 (m; 3H).

Example 4

Preparation of (7-phenyl-(5H,9H)-6,8-dioxabenzocyclohepten-2-yl)methanol

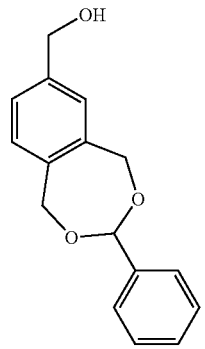

4 g of (3,4-bis-hydroxymethylphenyl)methanol (23.8 mmol), 40 ml of toluene, 3.06 g of benzaldehyde (28.5 mmol) and 0.24 g of Montmorillonite KSF (10 mg/mmol) are introduced into a flask equipped with a Dean-Stark. The medium is heated under reflux for 3 hours. After filtration, the toluene is evaporated under vacuum at 30° C. The residue is chromatographed on silica gel (heptane/ethyl acetate=7/3) to give 1.8 g of (7-phenyl)-(5H,9H)-6,8-dioxabenzocyclohepten-2-yl)methanol in the form of a white powder.

Yield=30% Melting point=113°-114° C. $^1$H NMR (DMSO d$_6$; 400.132 MHz) δ (ppm): 4.49 (d; 2H; J=5.6 Hz); 4.87 (d; 2H; J=14.1 Hz); 5.05 (dd; 2H; J=5.2 Hz and J=14.1 Hz); 5.18 (t; 1H; J=5.6 Hz); 5.97 (s; 1H); 7.21 (m; 3H); 7.38 (m; 3H); 7.45 (m; 2H).

Example 5

Preparation of (7,7-dimethyl-(5H,9H)-6,8-dioxabenzocyclohepten-2-yl)methanol

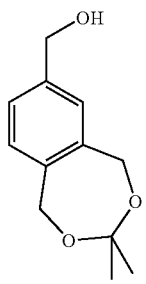

5 g of (3,4-bis-hydroxymethylphenyl)methanol (29.7 mmol), 25 ml of 2,2-dimethoxypropane (21.2 g; 0.2 mmol) and 0.29 g of p-toluenesulfonic acid (1.5 mmol) are introduced into a flask. After stirring for 1 hour 10 minutes at room temperature, the solvent is evaporated under vacuum at 30° C. and the crude product is chromatographed on silica gel (dichloromethane/methanol/aqueous ammonia=98/2/0.1). 5.98 g of (7,7-dimethyl-(5H,9H)-6,8-dioxabenzocyclohepten-2-yl)methanol are obtained in the form of a white powder.

Yield: 96% $^1$H NMR (CDCl$_3$; 400.132 MHz) δ (ppm): 1.52 (s; 6H); 4.6 (s; 2H); 4.87 (s; 4H); 7.08 (m; 2H); 7.18 (m; 1H).

Example 6

Preparation of 2-chloromethyl-7-(4-nitrophenyl)-(5H,9H)-6,8-dioxabenzocycloheptene

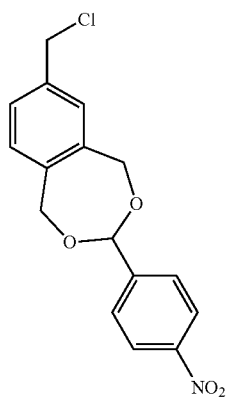

1.5 g (5 mmol) of [7-(4-nitrophenyl)-(5H,9H)-6,8-dioxabenzocyclohepten-2-yl]methanol in 15 ml of dichloromethane are introduced into a flask. 0.76 g (7.5 mmol) of triethylamine is added and 1 g (5.4 mmol) of p-toluenesulfonyl chloride is added in small solid portions at room temperature. After 20 hours of reaction, the solvent is evaporated off and the crude product is purified by silica gel chromatography (heptane/ethyl acetate: 4/1) to give 0.6 g of 2-chloromethyl-7-(4-nitrophenyl)-(5H,9H)-6,8-dioxabenzocycloheptene.

Yield: 38% Melting point: 138-140° C. $^1$H NMR (DMSO d$_6$; 400.132 MHz) δ (ppm): 4.76 (s; 2H); 4.93 (d; 2H; J=14.2 Hz); 5.14 (d; 2H; J=14.2 Hz); 6.14 (s; 1H); 7.34 (m; 3H); 7.73 (d; 2H; J=8.7 Hz); 8.25 (d; 2H; J=8.7 Hz).

Example 7

Preparation of methanesulfonic acid [7-(4-nitrophenyl)-(5H,9H)-6,8-dioxabenzocyclohepten-2-yl]methyl ester

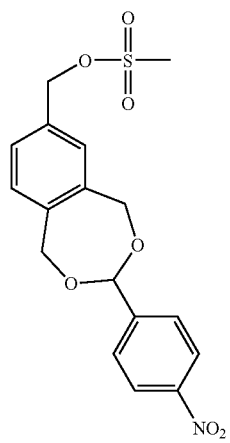

3 g (10 mmol) of [7-(4-nitrophenyl)-(5H,9H)-6,8-dioxabenzocyclohepten-2-yl]methanol in 50 ml of dichloromethane are introduced into a flask. 1.54 g (12 mmol) of diisopropylethylamine are added and 1.37 g (12 mmol) of mesyl chloride in solution in 10 ml of dichloromethane are added dropwise at −5° C. After 1 hour 30 minutes of reaction at −5° C., 20 ml of a 5% sodium bicarbonate solution are added, the phases are separated by decantation and the organic phase is washed with water. It is dried over sodium sulfate and the solvent is evaporated off. The crude product is purified by silica gel chromatography (heptane/ethyl acetate: 3/2) to give 0.6 g of methanesulfonic acid [7-(4-nitrophenyl)-(5H,9H)-6,8-dioxabenzocyclohepten-2-yl]methyl ester.

Yield: 16% $^1$H NMR (CDCl$_3$; 400.132 MHz) δ (ppm): 2.97 (s; 3H); 5.01 (m; 4H); 5.24 (s; 2H); 6.01 (s; 1H); 7.26 (m; 2H); 7.33 (dd; 1H; J=1.4 Hz and J=7.6 Hz); 7.77 (d; 2H; J=8.6 Hz); 8.26 (dd; 2H; J=1.8 Hz and J=7.0 Hz).

Each patent, patent application, publication, text and literature article/report cited or indicated herein is hereby expressly incorporated by reference.

While the invention has been described in terms of various specific and preferred embodiments, one skilled in this art will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A 7,7-disubstituted (5H,9H)-6,8-dioxabenzocycloheptene compound having the structural formula (I):

1.

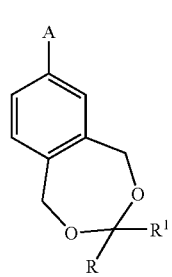

in which:
- A is a radical —CH$_2$—Y or a carboxaldehyde group —C(=O)H;
- Y is a halogen atom, a hydroxyl radical, a radical —OSO$_2$R$^2$, or a radical P(O)(OR$^3$)$_2$;
- R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group;
- with the proviso that R and R$^1$ may together form, with the carbon atom from which they depend, a ring member of 5 or 6 carbon atoms;
- R$^2$ is an alkyl radical or an aryl radical; and
- R$^3$ is an alkyl radical;

with the further proviso that R and R$^1$ cannot simultaneously be a methyl radical when A is the radical —CH$_2$OH; and the optical isomers thereof.

2. The compound as defined by claim 1, wherein formula (I) at least one of R or R$^1$ is not hydrogen.

3. The compound as defined by claim 1, having at least one methyl, ethyl, propyl, isopropyl, 2-methylpropyl, butyl, sec-butyl and/or tert-butyl radical substituent.

4. The compound as defined by claim 1, having at least one methoxy, ethoxy, propoxy, isopropoxy, butoxy, sec-butoxy and/or tert-butoxy radical substituent.

5. The compound as defined by claim 1, having at least one phenyl, naphthyl and/or pyridyl substituent.

6. The compound as defined by claim 1, wherein formula (I) R and R$^1$ together form, with the carbon atom from which they depend, a cyclopentane radical or a cyclohexane radical.

7. The compound as defined by claim 1, wherein formula (I) A is a radical —CH$_2$—Y, in which Y is a chlorine or bromine atom or a radical OSO$_2$R$^2$ or a radical P(O)(OR$^3$)$_2$, and R$^1$ is a hydrogen atom and R$^1$ is a nitrophenyl radical or vice-versa for R and R$^1$.

8. The compound as defined by claim 1, wherein formula (I) A is a radical —CH$_2$—Y, in which Y is a hydroxyl radical, and R is a hydrogen atom and R$^1$ is a nitrophenyl radical or vice-versa for R and R$^1$.

9. A method for preparing the compounds of formula (I):

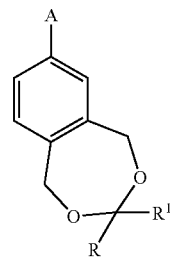

in which:
- A is a radical —CH$_2$—Y;
- Y is a radical P(O)(OR$^3$)$_2$;
- R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group;
- with the proviso that R and R$^1$ may together form, with the carbon atom from which they depend, a ring member of 5 or 6 carbon atoms; and
- R$^3$ is an alkyl radical;

comprising:
- in step 1, reducing a trialkyl ester of 1,2,4-benzenetricarboxylic acid in an aprotic solvent, to give (3,4-bis-hydroxymethylphenyl)methanol,
- in step 2, selectively protecting the two adjacent benzyl alcohol functional groups at the 3 and 4 positions of said (3,4-bis-hydroxymethylphenyl)methanol by reaction with a ketone or an aldehyde of formula R—CO—R$^1$ in an aprotic solvent, in the presence of a catalyst, to give the compounds of general formula (2):

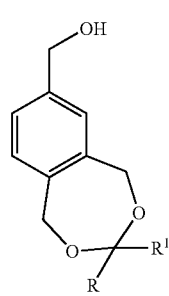

in step 3(a), converting the compounds of formula (2), by reaction with a derivative R$^2$SO$_2$Cl, into the compounds of formula (3):

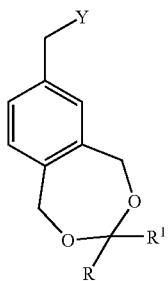

(3)

in which Y is a halogen atom, or a group —OSO$_2$R$^2$, in step 4, converting the compounds of formula (3) into the compounds of formula (5):

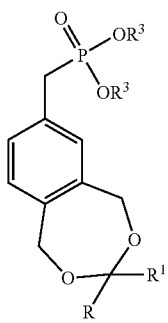

(5)

by reaction with a trialkylphosphite derivative P(OR$^3$)$_3$.

10. A method for preparing the compounds of formula (I):

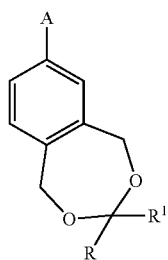

(I)

in which:
A is a carboxaldehyde group —C(=O)H;
R and R$^1$, which may be identical or different, are a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group;
with the proviso that R and R$^1$ may together form, with the carbon atom from which they depend, a ring member of 5 or 6 carbon atoms; comprising:
in step 1, reducing a trialkyl ester of 1,2,4-benzenetricarboxylic acid in an aprotic solvent, to give (3,4-bis-hydroxymethylphenyl)methanol,
in step 2, selectively protecting the two adjacent benzyl alcohol functional groups at the 3 and 4 positions of said (3,4-bis-hydroxymethylphenyl)methanol by reaction with a ketone or an aldehyde of formula R—CO—R$^1$ in an aprotic solvent, in the presence of a catalyst, to give the compounds of general formula (2):

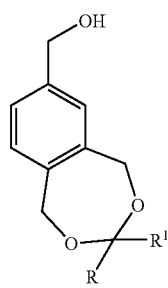

(2)

in step 3(b), oxidizing the compounds of formula (2) to give the compounds of formula (4):

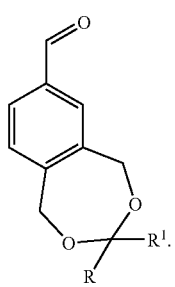

(4)

11. A compound having the following structural formula (2):

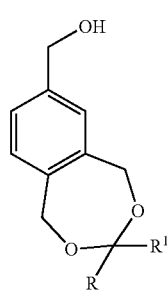

(2)

in which R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group, with the proviso that R and R$^1$ may together form, with the carbon atom from which they depend, a ring member of 5 or 6 carbon atoms and with the further proviso that R and R$^1$ are not simultaneously a methyl radical.

12. A compound having the following structural formula (3):

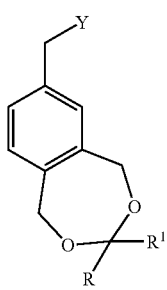

(3)

in which:

Y is a halogen atom, or a radical —OSO$_2$R$^2$,

R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group, with the proviso that R and R$^1$ may together form, with the carbon atom from which they depend, a ring member of 5 or 6 carbon atoms, and R$^2$ is an alkyl radical or an aryl radical.

13. A compound having the following structural formula (4):

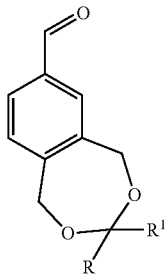

(4)

in which R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group, with the proviso that R and R$^1$ may together form with the carbon atom from which they depend, a ring member of 5 or 6 carbon atoms.

14. A compound having the following structural formula (5):

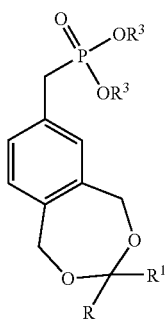

(5)

in which R and R$^1$, which may be identical or different, are each a hydrogen atom, an alkyl radical, an alkoxy radical, an aryl radical optionally substituted with one, two, three, four or five substituents selected from the group consisting of a halogen atom, the halogen being a chlorine, bromine, iodine or fluorine atom, an alkyl radical, an alkoxy radical, a cyano group and a nitro group, with the proviso that R and R$^1$ may together form, with the carbon atom from which they depend, a ring member of 5 or 6 carbon atoms and R$^3$ is an alkyl radical.

15. In a method for the synthesis of a non-steroidal analogue of vitamin D, the improvement which comprises, as a starting material reactant therefor, a compound of formula (I) as defined in claim 1.

16. The method for the synthesis of a non-steroidal analogue of vitamin D as defined by claim 15, said compound of formula (I) having the following structural formula (2):

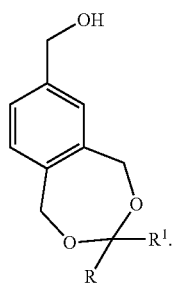

(2)

17. The method for the synthesis of a non-steroidal analogue of vitamin D as defined by claim 15, said compound of formula (I) having the following structural formula (3):

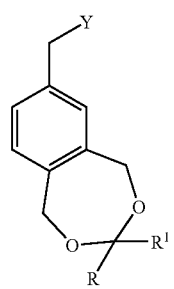

(3)

in which Y is a halogen atom, or a radical —OSO$_2$R$^2$.

18. The method for the synthesis of a non-steroidal analogue of vitamin D as defined by claim 15, said compound of formula (I) having the following structural formula (4):

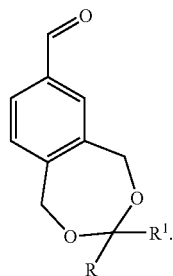

(4)

19. The method for the synthesis of a non-steroidal analogue of vitamin D as defined by claim 15, said compound of formula (I) having the following structural formula (5):

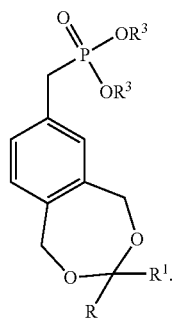

(5)

20. The method as defined by claim 15 for the synthesis of a non-steroidal analogue of vitamin D having the following structural formula (IV):

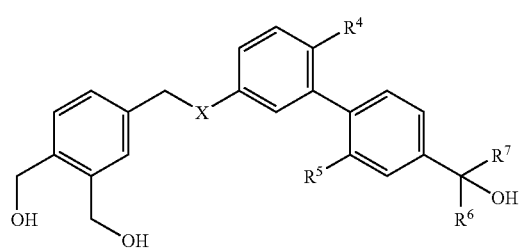

(IV)

in which:
- $R^4$ and $R^5$, which may be identical or different, are each a linear or branched alkyl radical having from 1 to 3 carbon atoms;
- $R^6$ and $R^7$, which are identical, are each a linear or branched alkyl radical having from 1 to 2 carbon atoms, hydrogenated or perfluorinated;
- X is —$CH_2$—, —NH—, —$NR^8$— or —O— and
- $R^8$ is a linear or branched alkyl radical having from 1 to 3 carbon atoms.

21. The method as defined by claim 20, comprising:

a) coupling a compound of formula (3):

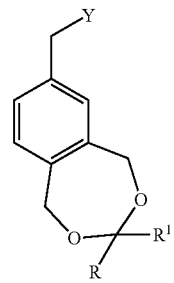

(3)

with a compound of formula (II):

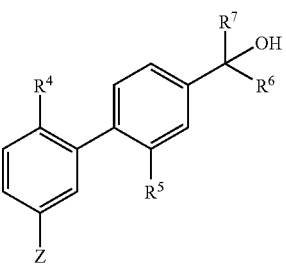

(II)

to produce a compound of formula (III):

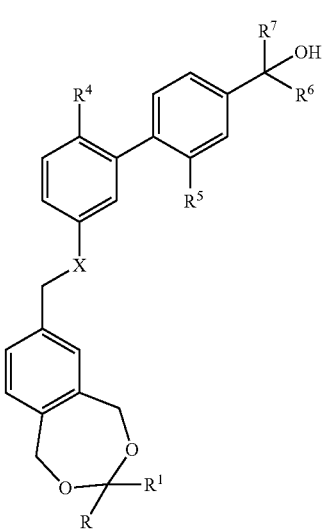

(III)

b) deprotecting two adjacent benzyl alcohol functional groups at the 3 and 4 positions contained in the (5H, 9H)-6,8-dioxabenzocycloheptene ring of the compound of formula (III), the said ring being obtained from the compound of formula (3), to produce a compound of formula (IV):

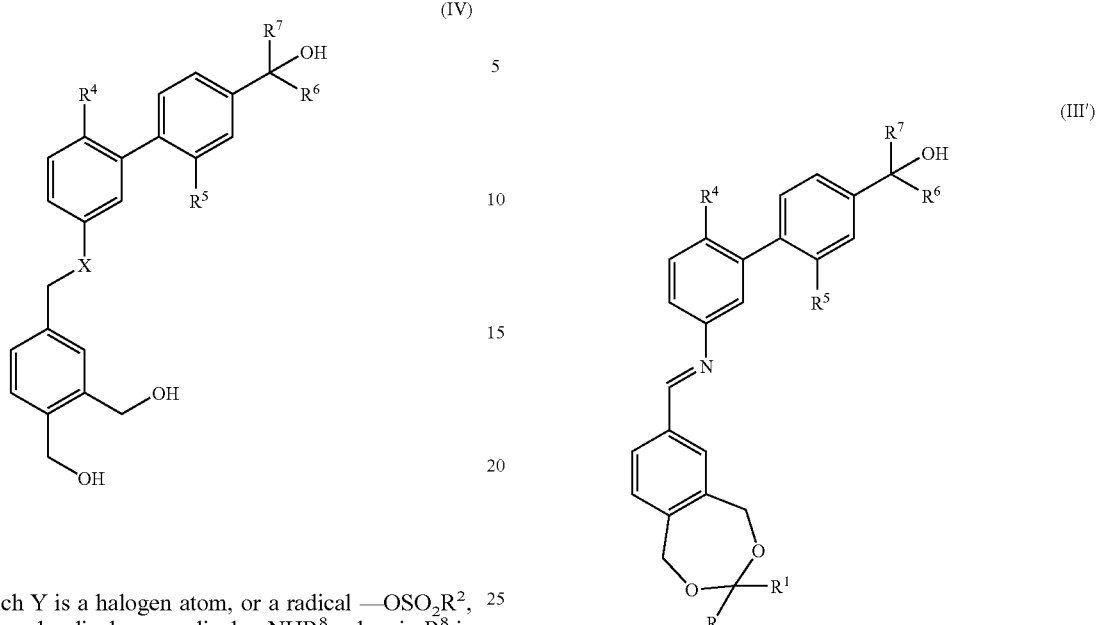

and in which Y is a halogen atom, or a radical —OSO$_2$R$^2$, Z is a hydroxyl radical, or a radical —NHR$^8$, wherein R$^8$ is a linear or branched alkyl radical having from 1 to 3 carbon atoms.

22. The method as defined by claim 15, comprising:
a) coupling the aldehyde functional group of a compound of formula (4):

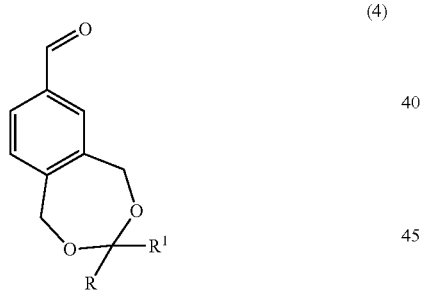

and the amine functional group of a compound of formula (II'):

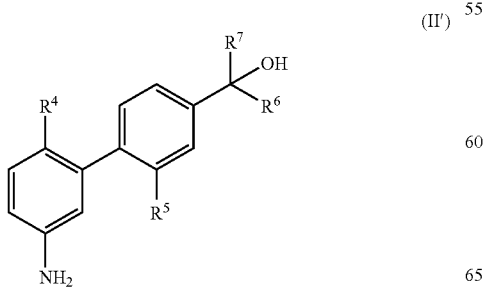

to produce a compound of formula (III'):

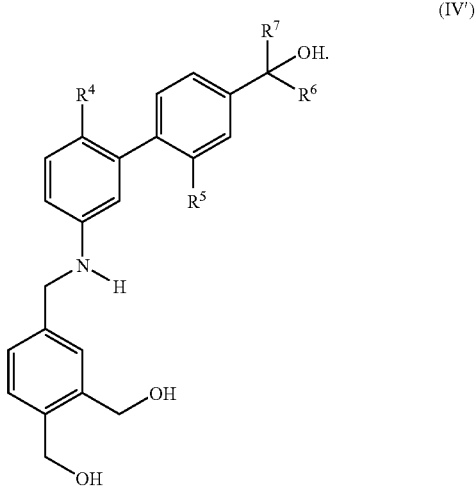

b) hydrogenating and hydrogenolyzing the compound of formula (III'), thus reducing the imine functional group and deprotecting the two adjacent benzyl alcohol functional groups at the 3 and 4 positions contained in the (5H,9H)-6,8-dioxabenzocycloheptene ring obtained from the compound of formula (4) (hydrogenolysis), to produce a compound of formula (IV'):

23. The method as defined by claim 15, comprising:
a) Horner-Emmons reacting a compound of formula (5):

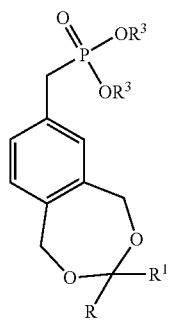

(5)

and a compound of formula (II''):

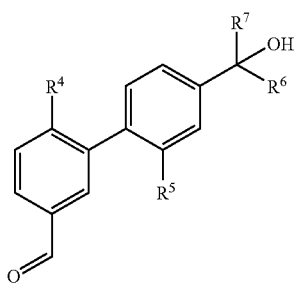

(II'')

to produce a compound of formula (III''):

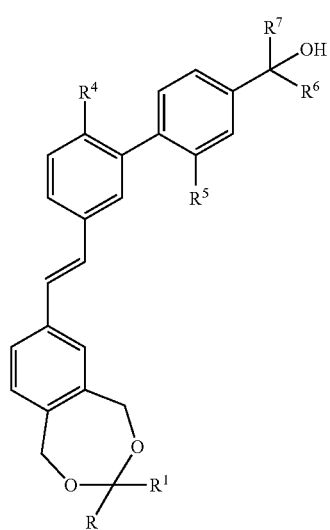

(III'')

b) hydrogenating and hydrogenolyzing the compound of formula (III''), thus reducing the double bond (hydrogenation) and deprotecting two adjacent benzyl alcohol functional groups at the 3 and 4 positions contained in the (5H,9H)-6,8-dioxabenzocycloheptene ring obtained from the compound of formula (5) (hydrogenolysis), to produce a compound (IV''):

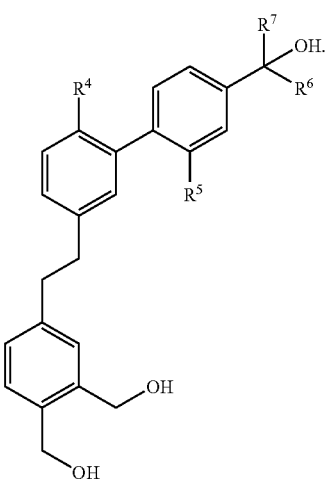

(IV'')

24. The method as defined by claim 20, comprising coupling a compound of formula (II):

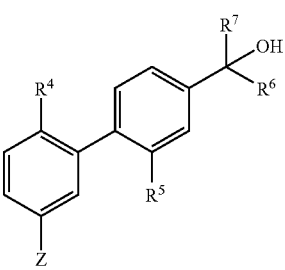

(II)

with a compound of formula (3):

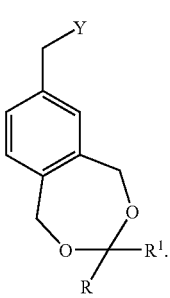

(3)

25. The method as defined by claim 15 for the synthesis of a non-steroidal analogue of vitamin D having the following structural formula (IV'):

26. The method as defined by claim 15 for the synthesis of a non-steroidal analogue of vitamin D having the following structural formula (IV''):

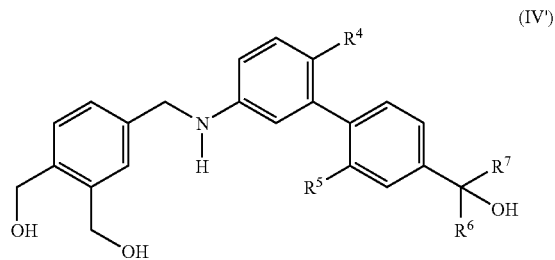 (IV')

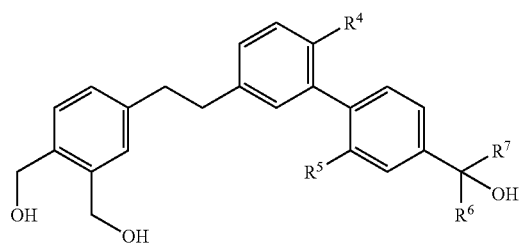 (IV'')

in which:
- $R^4$ and $R^5$, which may be identical or different, are each a linear or branched alkyl radical having from 1 to 3 carbon atoms;
- $R^6$ and $R^7$, which are identical, are each a linear or branched alkyl radical having from 1 to 2 carbon atoms, hydrogenated or perfluorinated, comprising coupling a compound for formula (II'):

in which:
- $R^4$ and $R^5$, which may be identical or different, are each a linear or branched alkyl radical having from 1 to 3 carbon atoms;
- $R^6$ and $R^7$, which are identical, are each an alkyl radical having from 1 to 2 carbon atoms, hydrogenated or perfluorinated, comprising coupling a compound of formula II'':

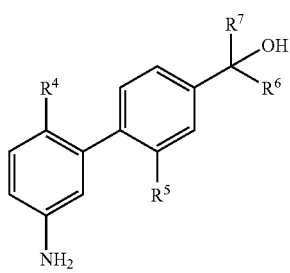 (II')

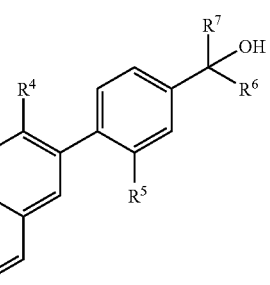 (II'')

with a compound of formula (4):

with the compound of formula (5):

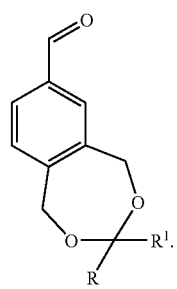 (4)

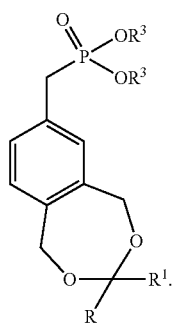 (5)

* * * * *